United States Patent [19]

Weferling

[11] Patent Number: 4,781,867

[45] Date of Patent: Nov. 1, 1988

[54] PROCESS FOR MAKING PHOSPHINIC OR PHOSPHONIC ACID CHLORIDES

[75] Inventor: Norbert Weferling, Hürth, Fed. Rep. of Germany

[73] Assignee: Hoechst Aktiengesellschaft, Frankfurt am Main, Fed. Rep. of Germany

[21] Appl. No.: 122,924

[22] Filed: Nov. 19, 1987

[30] Foreign Application Priority Data

Nov. 26, 1986 [DE] Fed. Rep. of Germany ....... 3640357

[51] Int. Cl.$^4$ .............................................. C07F 9/52
[52] U.S. Cl. ................................................. 260/543 P
[58] Field of Search ..................................... 260/543 P

[56] References Cited

U.S. PATENT DOCUMENTS 4,536,350 8/1985 Weferling ........................ 260/543 P

FOREIGN PATENT DOCUMENTS 1138770 10/1962 Fed. Rep. of Germany .
2335371 1/1975 Fed. Rep. of Germany .
3235787 3/1984 Fed. Rep. of Germany .

OTHER PUBLICATIONS

Houben Weyl, *Methoden der Organischen Chemie*, Suppl. to 4th Ed., Georg Thience Verlag, Stuttgart, vol. E2, 1982, pp. 150–165, 326–333.

Suminov, S et al. Zh Vses. Khim Obshchest 17(2) 234–6, 1972 CA 77(11): 74597m.

*Primary Examiner*—Paul J. Killos

[57] ABSTRACT

Phosphinic or phosphonic acid chlorides are made by reacting a primary or secondary phosphine with sulfuryl chloride.

5 Claims, No Drawings

PROCESS FOR MAKING PHOSPHINIC OR PHOSPHONIC ACID CHLORIDES

This invention relates to a process for making phosphinic or phosphonic acid chlorides of the general formulae

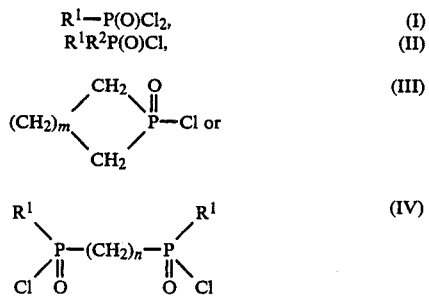

$$R^1\text{—P(O)Cl}_2, \quad (I)$$
$$R^1R^2\text{P(O)Cl}, \quad (II)$$

(III)

(IV)

in which
R$^1$ and R$^2$ each stand for a linear or branched alkyl group, a substituted or unsubstituted aryl or cycloalkyl group having 1 to 16 carbon atoms,
m stands for 2 or 3,
n stands for a whole number of 1 to 6,
and one of the hydrogen atoms in formula III may be a methyl or ethyl group.

Various processes for making phosphinic acid or phosphonic acid dichlorides have already been described, e.g. in Houben-Weyl "Methoden der Organischen Chemie", Georg Thieme Verlag, Stuttgart, New York 1982, vol. E2, pages 150–165, 326–333. It is also known that phosphinic oxide to treatment with chlorine in the presence of hydrogen chloride (cf. German Specification DE-Al No. 23 35 371), or by reacting a phosphine oxide with hexachloroethane (cf. German Specification DE-Al No. 32 35 787).

These prior art methods are not fully satisfactory however inasmuch as the feed materials used therein are phosphine derivatives which are required to be initially made from the phosphines.

The present invention now unexpectedly provides a process which we believe in the first to permit a primary or secondary phosphine to be used to feed material and the phosphinic acid or phosphonic acid chlorides of general formulae I to IV above to be directly obtained, which comprises: reacting sulfuryl chloride with a primary or secondary phosphine of the general formulae $$R^1HP\text{—H}, \quad (V)$$

$$R^1R^2P\text{—H}, \quad (VI)$$

(VII)

or (VIII)

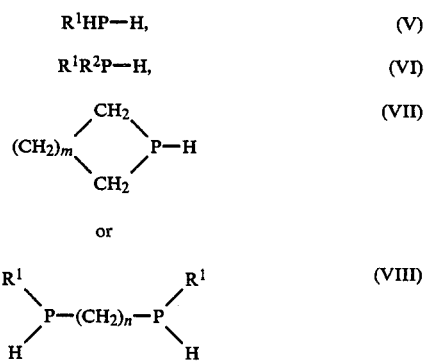

in which R$^1$, R$^2$, m and n have the meanings given above, and one of the hydrogen atoms of the CH$_2$-groups in formula VII be a methyl or ethyl group.

Further preferred and optional features of the invention provide:
(a) for the sulfuryl chloride to be reacted with the primary phosphine in a molar ratio of at least 3:1, and with the secondary phosphine in a molar ratio of at least 2:1;
(b) for the reaction to be effected at temperatures between −60° C. and +90° C.;
(c) for the reaction to be effected in the presence of a solvent and
(d) for the solvent to be sulfuryl chloride in excess or a standard aliphatic or aromatic solvent, e.g. a hydrocarbon or aprotic solvent.

EXAMPLE 1

Preparation of dimethylphosphinic acid chloride

A solution of 295 g (2.2 mol) SO$_2$Cl$_2$ in 100 ml hexane was introduced into a 500 ml multineck flask provided with a stirrer, reflux condenser and thermometer. The solution was cooled to 0° C. and dimethylphophine was added so rapidly that the internal temperature failed to exceed 10° C. 62 g (1 mol) dimethylphosphine was so introduced within 90 minutes. Next, the yellow reaction mixture was heated to boiling temperature (about 70° C.) which permitted residual gaseous reaction products to be expelled. The clear, henceforth red solution was allowed to cool and (CH$_3$)$_2$P(O)Cl was found to crystallize out. It was purified by removing all of the low boilers under vacuum and dissolving the solid residue in about 150 ml boiling hexane. The product which was crystallized out while cold, was separated via a reversing frit and dried.

The yield was 96 g, or 86% of the theoretical. The product was subjected to NMR-spectroscopy and found to be clean; δP=59.5 ppm (>99%); literature value: 62.8 ppm.

EXAMPLE 2

Preparation of sec.-butylphosphonic acid dichloride

A solution of 90 g (1 mol) sec.-butylphosphine in 90 g toluene was admixed dropwise within 1 hour with 440 g (3.3 mol) sulfuryl chloride. In order to maintain the reaction temperature between 20° and 30° C., it was necessary during the first third of the introduction period, for the glass flask to be cooled from the outside by means of a methanol/dry ice freezing mixture. To initiate the post-reaction, the whole was heated to 60° C. and stirred until gas ceased to be evolved. All of the low boilers were removed under vacuum at room temperature. The crude product was distilled.

bp: 88°–91° C.; yield: 148 g (84%)

δP=57.9 ppm (>99%)

Di-n-butylphosphinic acid chloride (Example 3), n-octyl-phosphinic acid dichloride (Example 4), and dicyclohexylphosphinic acid chloride (Example 5) were made in a manner analogous to that described in Examples 1 and 2 (cf. Table).

TABLE

| Ex. | Phosphine g mol | SO$_2$Cl$_2$ g mol | Solvent | Reaction temperature | Reaction period | Yield g % | $^{31}$P-NMR ppm |
|---|---|---|---|---|---|---|---|
| 3 | 146/1 | 281/2.1 | hexane | 20–80° C. | 2 h | 168/85 bp 135° C./0.1 mbar | 70.7 |
| 4 | 87/0.68 | 286/2.1 | — | −10–+10° C. | 2 h | 108/78 bp 80° C./0.1 mbar | 49.1 |
| 5 | 198/1 | 297/2.2 | toluene | 25–60° C. | 4 h | 207/83 (from hexane) | 81.1 |

We claim:

1. A process for making phosphinic or phosphonic acid chlorides of the general formulae $$R^1-P(O)Cl_2, \quad (I)$$
$$R^1R^2P(O)Cl, \quad (II)$$

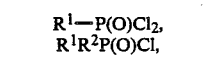
(III)

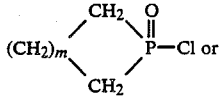
(IV)

in which
R$^1$ and R$^2$ each stand for a linear or branched alkyl group, a substituted or unsubstituted aryl or cycloalkyl group having 1 to 16 carbon atoms,
m stands for 2 or 3,
n stands for a whole number of 1 to 6,
and one of the hydrogen atoms in formula III may be a methyl or ethyl group,
which comprises: reacting sulfuryl chloride with a primary or secondary phosphine of the general formulae $$R^1HP-H, \quad (V)$$
$$R^1R^2P-H, \quad (VI)$$

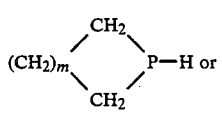
(VII)

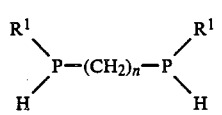

in which R$^1$, R$^2$, m and n have the meanings given above, and one of the hydrogen atoms of the CH$_2$-groups in formula VII may be a methyl or ethyl group.

2. The process as claimed in claim 1, wherein the sulfuryl chloride is reacted with the primary phosphine in a molar ratio of at least 3:1, and with the secondary phosphine in a molar ratio of at least 2:1.

3. The process as claimed in claim 1, wherein the reaction is effected at temperatures between −60° C. and +90° C.

4. The process as claimed in claim 1, wherein the reaction is effected in the presence of a solvent.

5. The process as claimed in claim 4, wherein the solvent used is sulfuryl chloride in excess or a standard aliphatic or aromatic solvent.

* * * * *